US008900138B2

(12) United States Patent
Horvath (10) Patent No.: US 8,900,138 B2
(45) Date of Patent: Dec. 2, 2014

(54) HEADLIGHT APPARATUS AND METHOD (76) Inventor: James P. Horvath, Redlands, CA (US)

( * ) Notice: Subject to any disclaimer, the term of this patent is extended or adjusted under 35 U.S.C. 154(b) by 316 days.

(21) Appl. No.: 12/590,384

(22) Filed: Nov. 5, 2009

(65) Prior Publication Data

US 2011/0105851 A1 May 5, 2011

(51) Int. Cl.
- A61B 1/06 (2006.01)
- H05B 41/02 (2006.01)
- F21V 8/00 (2006.01)
- A61B 19/00 (2006.01)
- F21V 21/084 (2006.01)
- A61B 19/02 (2006.01)

(52) U.S. Cl.
CPC ............ *A61B 19/5202* (2013.01); *G02B 6/0008* (2013.01); *A61B 2019/5206* (2013.01); *A61B 2019/262* (2013.01); *H05B 41/02* (2013.01); *F21V 21/084* (2013.01); *A61B 2019/0259* (2013.01)
USPC .......................................................... 600/249

(58) Field of Classification Search
USPC ............................ 600/249; 362/103, 572, 804
See application file for complete search history.

(56) References Cited

U.S. PATENT DOCUMENTS 3,285,242 A * 11/1966 Wallace ........................ 600/249
3,775,606 A * 11/1973 Bazell et al. .................. 362/552
5,412,749 A * 5/1995 Sayegh et al. ................. 385/115
5,898,290 A * 4/1999 Beard et al. ................... 307/150
2007/0236955 A1 10/2007 Fowler
2008/0085111 A1 4/2008 Fowler
2009/0168433 A1* 7/2009 Frick ............................. 362/298

OTHER PUBLICATIONS

"Right Light Lifts Fatigue and Concentration,"European Hospital, Mar. 1, 2005, pp. 1-2, European Hospital Verlags GmbH, http://www.european-hospital.com/en/article/397-Right light lifts fatigue and concentration.html.

* cited by examiner

Primary Examiner — Christian Sevilla
(74) Attorney, Agent, or Firm — Cislo & Thomas, LLP (57) ABSTRACT A portable headlight assembly for illuminating a surgical site and moves with the surgeon, the headlight assembly having a headlight source, such as a HID lamp, to illuminate via a light cable coupled to receive and transmit the illumination in the range of natural daylight between 5000 and 6700 degrees Kelvin, a power supply that couples to the HID lamp when the light cable is located to receive focused light from it, and a control that monitors the operation of the headlight source and the portable power supply and is responsive to temperature of the portable power supply and radiation supplying illumination. The light cable extends between the HID lamp to guide illumination from the HID lamp and its reflector to a lens carried on a head strap worn by a practitioner for delivering the illumination to the surgical site.

13 Claims, 9 Drawing Sheets

HEADLIGHT APPARATUS AND METHOD

CROSS-REFERENCE TO RELATED APPLICATIONS

STATEMENT REGARDING FEDERALLY SPONSORED RESEARCH

SEQUENCE LISTING

BACKGROUND OF THE INVENTION

The circular mirror with a centered hole to look through that doctors and dentists, herein practitioners, wore to reflect ambient room light toward the patient was low cost but dependent on available light thus ineffective. Those were compact, lightweight and relatively low tech. Studies have been made of the best electrical light and how to deliver that to the surgical site so the practitioners can easily see the work to be done. So far the common practice is an overhead light that can be angled to aim it toward the area of concern, interest and surgery. Those overhead lights have to be adjusted and readjusted. The practitioner touches them so they have small protective antiseptic booties over their handles and require the aversion of the eyes from the patient to the light during the readjustments. also they are substantially spaced from the surgical site and thus need to be high wattage and focused to put illumination just where required so the practitioner typically has to look back and forth between the light and the surgical site. a light that always shines on the surgical site where the practitioner is working and looking would reduce the interruptions in concentration and focus on the medical procedure being performed is needed.

Studies show psychological effects of good illumination on the visual acuity and success of endeavors. Melatonin hormone controls the circadian rhythm and the performance of animals and humans. In periods of darkness, melatonin reduces cardiovascular activity and induces fatigue. Morning light inhibits melatonin secretion in the pineal gland, which increases cardiovascular activity. Melatonin inhibition peaks at 450 nm in the continuous visual spectrum, i.e. in the blue spectral range. Light containing a large proportion of blue wavelengths therefore inhibits the secretion of melatonin in the pineal gland. If these blue wavelengths are absent (reddish light), melatonin secretion is uninhibited, which produces fatigue, recent research, lead by Professor Dietrich Gall, head of the Lighting Technology Department, at Ilmenau University of Technology, Germany, with the cooperation of the lighting firm Berchtold GmbH & Co. KG, of Tuttlingen, in the USA Berchtold Corporation□1950 Hanahan Road□Charleston, S.C. 29406□ analyzed lighting as a form of radiation and the potential psychological effects of its dose level on doctors, dentists and surgeons.

Consequently, light having the proper wavelengths and intensity and aimed at the area of doctor effort and scrutiny is of paramount importance for a successful and good result and often may be life saving. Past efforts to illuminate a surgical site or area of concern and investigation by the practitioner have been less than compact, portable, safe and reliable in performance.

In 2002, Professor Gall succeeded in describing the circadian effect of light in mathematical terms, defining the circadian effect coefficient (acv coefficient) as the ratio between the visual utilization effect (taking the photoreceptors' effect curve into account) and the circadian utilization effect (taking the effect curve of the circadian retinal receptors into account). So it became possible to measure the circadian effect of light, and provide a simple means to describe the physiological effect of light. Volker Dockhorn, engineer and Product Manager, OR-Lights, Berchtold, explained that the goal was to determine whether surgical lights of different color temperatures produced different physiological effects on a surgeon, and use that knowledge to deliberately reduce fatigue and improve their wakefulness when working at night. Since 1929, CHROMOPHARE® lights have led the market in surgical equipment technology. Quality surgical lighting illumination and consultant's knowledge of efficient and versatile operating room design set BERCHTOLD apart in the market. CHROMOPHARE® X 65:Tn: 4300 K—acv undimmed: 0.60—acv dimmed: 0.60—remark: opto-mechanical dimming. CHROMOPHARE® D 650 plus Tn: 4300 K—acv undimmed: 0.59—acv dimmed: 0.51—remark: electronic dimming. Comparative light Tn: 3400 K—acv undimmed: 0.45—acv dimmed: 0. Results of measurements of the circadian effect coefficient for three surgical lights all lights were first measured at an luminance of 100,000 lux and subsequently with luminance dimmed to 50% Table 1 presents results of measurements of the circadian effect coefficient (acv coefficient) for three surgical lights, one gas discharge light (BERCHTOLD® CHROMOPHARE® X 65), one halogen light with a high color temperature of 4,300K (BERCHTOLD® CHROMOPHARE® D 650plus) and one halogen light of comparable size, from another firm, with a lower color temperature of 3,400K and a large red component. All lights were first measured at a luminance of 100,000 lux and subsequently with luminance dimmed to 50%.

The results described would suggest that the gas discharge light CHROMOPHARE® X 65 and the halogen light CHROMOPHARE® D 650plus, with its high color temperature (4,300K), cause less fatigue, whereas it would be expected that surgery performed under a halogen light with a lower color temperature (3,400K) would cause greater fatigue, especially at night.

To verify this outcome, the study examined the performance and concentration of 55 participants. In one group, 30 people carried out tests in winter; in the other, 25 performed them in summer, to determine seasonal effects. Experiments were limited to a study of the difference in effect between the two-halogen lights, which initially irradiate a similar spectrum. The color temperature difference between the two lights arises through selective filtering of the wavelength spectrum by light manufacturers.

The irradiated surface was flat, and its reflectivity was therefore higher (76%) than is usually the case with human tissue. For this reason the luminance of both lights was adjusted to 40,000 lux, by altering the size of the light field. The light field diameter was the same for both. The acv value for the halogen light with high color temperature was 0.59, while for the one with lower color the temperature was 0.45, said Volker Dockhorn.

The participants did not know which lights were being used. To induce a general state of fatigue, such as results through mental work, the participants were asked to solve arithmetical problems under time pressure. Then the d2 test was performed, to determine a subject's performance capability and power of concentration. The sequence in which the lights were used was altered from one test to the next. 50% of participants began the tests under the light with high color temperature (BERCHTOLD®), then, following an adaptation interval, performed them under the light with lower color temperature. The remaining 50% began tests under the reference light. On average, participants working under the BERCHTOLD® light answered 502 questions; those working under the reference light answered only 485 questions, equivalent to a 3.5% improvement in performance by those working under the BERCHTOLD® light. Statistical error probability was 0.069 in this case, i.e. only slightly short of the significance threshold (0.05), and it is therefore justified to point to a trend.

If, as a means to determine power of concentration the number of questions answered correctly is considered, the difference was even more pronounced. On average, under the BERCHTOLD® light 205 questions were answered correctly, whereas under the reference light 195 questions were correct an average, 5.1% lower than in the case of the reference light. The result has an error probability of 0.041, i.e. within the significance threshold of 0.05. Therefore, in winter, a significant increase in power of concentration and a decrease in error frequency were found in work performed under the BERCHTOLD® light with a high color temperature of 4,300K.

The scientists presume that the results would diverge even more if the tests were carried out at night, when melatonin blood levels are higher. However, as it was, even tests carried out during the afternoon or evening showed a clear trend and, in some part, also significant results that appear to confirm the results of the physical measurements.

Thus the study has proved that a high color temperature of 4,300 as irradiated by a CHROMOPHARE® D 650 plus light can enhance a surgeon's performance capability during the winter (trend). Work performed under a surgical light of low color temperature (3,400 K) is subject to a significantly greater error frequency. During night surgery, when a surgeon's melatonin blood level is high, this effect is thought particularly pronounced.

Headlight assembly United States Patent Application number 20070236955 and discloses portable fan cooled light with optics for surgery. That teaching is missing is the importance of maintaining color temperature ideal for a surgeon to see different anatomical structures and reduce fatigue. In the background thereof it includes, one problem associated with known dental loupe lights is that the housing of the light source is typically secured to a bench adjacent the dental professional so as to be fixed, i.e., stationary and immobile. The mounting is needed due to the size and design of that headlight and cooling fan. By being fixed or having poor design, the movement of the dental professional is hampered and restricted during dental procedures. additionally, the length and fixed headlight end or proximal plane of the fiber optic cable disclosed would no doubt impede the ability of the dental professional to move or manipulate various instruments during the dental procedure, which can result in the fiber optic cable being damaged or otherwise compromised.

Any light source capable of proper illumination will consume a significant amount of energy and create heat. The light source used in conjunction with the fiber optic cable and any focusing optics can provide a single defined beam that does not interfere with its use. The light source can be configured to emit light characterized as substantially 5500 Degrees Kelvin or "noon day" sunlight. Accordingly, the light emitter can include a plurality of LEDs that cooperate to emit the light. Alternatively, the light emitter can include a halogen, HID, or other lamp that can be filtered so as to emit the light. HID lights have no filament to burn up so they last ten times longer that common halogen lamps. The lamp is filled with xenon gas that is excited by high voltage 20,000 volts direct current creating light intensity equivalent to daylight 6000 Degrees Kelvin in color temperature. another benefit is that only 2.9 amperes are required using about 35 watts. a ballast and igniter are required to energize 12 volts to the high voltage needed for the excitation of the xenon. Optimization of low power lamp achieving an average used illumination output with performance equivalent to a 300-watt xenon lamp by reducing overall radio frequency infrared output reducing shielding required when plugged into a wall unit while also reducing the heat and safety concerns. Light output is comparable to a stand 300-watt xenon unit that is plugged into the wall using the wall circuitry for its shielding and cooling. The disclosed battery powered unit has the ability to be flexible enough to be un-tethered allowing freedom of movement with its compact portable design configuration and minimized shielding needs releases it from being plugged into the wall. The high wattage system used in a interior or minimally invasive hip procedures with a plugged in unit is often placed under the surgical table covered and separated with a sterile draped to maintain a sterile field increases the chance of fire as compared to the presently disclosed belt worn battery low wattage that does not have that risk and also enables the user to move about freely without assistance. The disclosed cordless headlight assembly may be carried within a personal environmental surgical suit primarily used by orthopedic surgeons while performing hip and joint surgeries allowing them to move around the surgical table when they need to articulate body parts. More progressive surgeons move the plug-in versions under the table requiring a nurse to reach underneath the table plug and unplug the headlight fiber optic cable. also by having the cords and cables at their feet movement of the two surgeons working side-by-side causes them to step on the cables cause damage. The disclosed portable unit in surgery permits ease of movement and no incidence of damage to the cables as they are carried by the surgeon(s) out of harm's way. The plug in fiber optic cables can fall into the sterile field during surgery compromising the sterility of the procedure. Using the disclosed fiber optic headlight eliminates that even when using the environmental helmet or the stand headlight version.

Furthermore, the cooling of lighting devices that typically generates a substantial amount of heat has resulted in its placement being fixed and/or remote from the loupe columniation lens. In part, this is because the heat generated from the light source has caused its housing to become hot, which will injure the practitioner or assistant that comes too close or accidentally touches the hot housing accordingly, that patent application teaches and explains that there is a benefit of a lighting apparatus that includes a headlight that is thermally disconnected from the light source and fan housing. Even though, that patent application recognizes as beneficial for the lighting apparatus to include a cooling apparatus so that the temperature of the light source housing would be held below a potentially dangerous or harmful temperature, that has not been refined to the level of the present disclosure of a compact portable headlight assembly as will be disclosed. Not appreciated or understood in that patent application are the benefits of a surgical site illumination with various components, housed together in proximity and wherein the light is selectively directed into the optic fiber cable. Furthermore, it would be beneficial for the apparatus to be portable and/or usable with the optic fiber cables of various lengths and loupes that are also interchangeable as needed. The light source can be any lamp that emits light. Such a lamp can be a halogen lamp, high intensity discharge (HID) lamp, array of light emitting diodes, LEDs, etc. Operating rooms in many hospitals lack floor space for added new technology including important instrumentation. The disclosed surgical headlight offers a compact solution. Removal of large high wattage headlight would revolutionize the way that surgical headlights are used in the operating room. The disclosed compact portable high light configuration meets the needs of the surgeons and is low wattage but with sufficient illumination of the surgical site.

An example of a light source can be found in U.S. patent application Ser. No. 11/339,288, which is incorporated herein in its entirety by specific reference notes the spectrum or color temperature of the light emitting diodes of the light source can be tuned. This allows for the spectrum or temperature of the light to be adjusted as desired or needed. For example, the spectrum of light emitted by the light source may deviate from the noonday sunlight spectrum about 5200 Degrees Kelvin to about 6600 Degrees Kelvin over time, and tuning the spectrum can re-achieve the desired spectrum. also, the spectrum can be tuned and adjusted during manufacturing. alternatively, there may be situations where light that does not approximate the noonday sunlight spectrum is desired or needed, where tuning may alter the spectrum away from noonday sunlight. In addition, the color-rendering index produced with the present invention is significantly improved compared to conventional devices and the resulting light spectrum can more closely simulate noonday sunlight. as such, the spectrum can be characterized as being from about 5200 Degrees Kelvin to about 6600 Degrees Kelvin, more preferably from about 5400 Degrees Kelvin to about 6000 Degrees Kelvin, and most preferably about 5500 Degrees Kelvin. Notably there is no teaching of portable cooled high intensity discharge lamps in this application or the importance of lighting safely anatomical structures with safety and freedom of movement available to a practitioner.

Portable headlight assembly of United States Patent Application 20080085111 adds a camera to the concept and mentions a high intensity discharge lamp but it still does not address portability and safety.

SUMMARY OF THE INVENTION

Portable high intensity headlight system overview includes portable light source assembly in a housing, a headset, fiber optic light cables, a charging station, a support belt, a support holster, cable brackets, a headset bracket and a rolling stand. The portable headlight assembly consists of a power supply including a self-contained battery, a powered lamp assembly with a fan cooling system, a battery charge level display indicator or battery charge gauge, a charging terminal and a light cable connector activator. The headset consists of an adjustable headband with a magnifying lens. The fiber optic light cable may consist of be multi optic fibers and can be assemblies of different lengths. Those assemblies of different lengths match configurations to cooperate with the portable headlight assembly and headset. a short cable for a belt mount configuration of the portable headlight assembly, medium cable for a side holster configuration of the portable headlight assembly, long cable for a rolling stand support of the portable headlight assembly are to extent between the practitioner's head and the portable headlight assembly. The disclosed system has a lightweight, compact and efficient fiber optic cable approximately 10-20% lighter than plug in models. The belt support of the fiber optic cable at the base of the gown via a clip relieves loads normally associated with the traditional plug in fiber optic light systems with a 8-10 ft cables that couple to a box. The disclosed headlight cable relieves a dramatic amount of surgeon stress and fatigue. The disclosed system allows for freeing up floor and table space in the operating room and does not require any support equipment to be in the operating room traffic areas or under foot. The disclosed battery powered surgical system minimizes surgical contamination of the sterile field by reducing the exposure of the fiber optic cable. Often when using a larger cable when moving around the table the cable will be dragged across surgical trays contaminating both tools, instruments and fittings at substantial cost time delay in surgery. In the disclosed portable system the fiber optic cable is run under the surgical gown not exposed at any time as the whole unit is worn under the gown. If the surgeon were to turn around it would not cross into the sterile field and cause undue delays and hazards. The risk of contamination caused by the use of the disclosed lamp is dramatically reduced. The disclosed system having a lamp module independent of any other components can be placed into a charger, teamed with a fiber optic cable headset or with an environmental space helmet suit depending on the procedure. The function while being used in the operating room allows surgeons to leave the operating room, move from table to table or computer or to fluoroscope for identification purposes without relying on support staff to plug or unplug for each move. The surgeons get to focus on the procedure rather than if he needs to be plugged or unplugged, clipped or unclipped or any of the other problems that may include constant yanking of the fiber optic cables due to use of plugged in head lights eliminating unexpected cable trampling in the usual crowding of the typical operating room. The carrying of the portable headlight assembly fan and light is safe because the temperature of the housing though warm is never hot and in the air-conditioned surgical suite where ambient room temperature is 70 F. The surgeon appreciates any warmth from the fan that is carried on a belt and against his/she's body. In addition to the stress of concentration required of the surgeon during surgery as causes for fatigue the operating room temperature of approximately 19 to 21 C or 66 to 68 F degrees for sustained periods of time. Back fatigue in the circulating cold air while in a relatively fixed position for 2 to 8 hours normally in not including any wind chill factor from Laminar air flow technology or gross flow used in most operating rooms to remove stale air and odors. Surgeons after putting portable HID surgical headlight system on said that after wearing for 5 minutes they had not even noticed that they were wearing anything at all. It freed up mobility around the patient the operating room making them more efficient saving valuable time for them minimizing the patient's time in surgery. The charging station consists of a charging base lamp retainer, charging controller board, charge indicator and contact terminal board. The charging base includes two charging stations with contact terminal and charge indicator. The charging station can be combined for multi charger application or for mounting on a rolling stand. The charging base has attachments for different length cable brackets one on each side and a threaded hole in bottom for attachment to the rolling stand. The disclosed system assists the surgeon's operating room comfort allowing them to stay independent in more or less a fixed position or walk back forth in a cool environment roughly 62-68 F degrees for extended periods of time. The back support by the disclosed belt offers some surgeon back stability and lower lumbar assistance. The disclosed unit produces approximately 100 F airflow underneath the surgeon's gown, which allows for removal of moisture with a slight warming effect but without the saturation of the air temperature affecting and stiffening back muscles during surgery. Surgeons have reported being exceptionally hot in surgery and so use ice packs to regulate their temperature but there was no need with the disclosed system. In using the unit they reported just the airflow decreased their perspiration dramatically improving their overall comfort in a positive way. The belt cooling system substantially increased the surgeon's comfort underneath the gown. In addition to the overall comfort level of the belt unit surgeons have reported that after five minutes they forget they even have the belt on so the dynamics of how the surgeons perform are changed by eliminating annoying inconveniences of plug in units that require relying on someone to turn on or off or replace or unplug for the surgeon to walk out of the operating room.

The specifics of the preferred charging will be briefly described. The 110V to 18V converter is a certified UL 60601-2 approved transformer that plugs into the wall and electrically couples and delivers direct current to a charging base. This configuration is preferably only used for charging when the portable headlight assembly is not in use. The support belt surrounds the waist for ventilation of the practitioner; there is a pocket to hold the portable headlight assembly and direct intake and exhaust air out away from practitioner. The intake and exhaust will have an integral support to hold and control flow thru ducts. The support holster consists of a thin waist belt supporting the portable headlight assembly holster on either the practitioner's left or right thigh via Velcro hooks and loops on conjugating portions of the thigh strap. The cable bracket has a support hoop with fitted plugs to protect fiber optic cable when the wrapped around ends thereof are plugged together. HID (High Intensity Discharge) achieves a very small and high intensity point of light by minimizing the arc gap as compared to higher output HID bulbs. Maximizing efficiency drawing about 0.80 amperes producing 12 watts with a CCT (correlated color temperature) of 6000-6700 K at the lamp. The arc ignition is excited by a high voltage approx 20,000 volts direct current through a HID lamp. The rolling stand consists of a tubular pole with multiple wheels and attachments to conjugate by threads with the charging station base and it also holds headsets and belts. It will allow operator to use stand as charging bracket or when unplugged to use stand as the portable headlight assembly rolling bracket when in use.

The preferred portable headlight assembly has a self contained lithium ion polymer battery power supply and a lamp preferably having a metal halide lamp in the class of high pressure, high intensity discharge (HID) lamp which differs from halogen, incandescent, fluorescent of light emitting diode (LED) illuminating sources. The disclosed headlight system provides the color of light and quality of light to illuminate wounds comparable to stand fiber optic surgical headlamps. The columniation color of the light was perceived superior and exceptional although not as intense as the stand but well within their normal operating needs. If the extra intensity of light were required for 10-15% of their surgeries, surgeons could use the stand plug in version. In comparison to the provided overhead surgical lamps the light beam appears to be approximately 15-20% brighter than total columniation output of the overhead surgical lights with the versatility of focusing that columniation light into deep wounds to be able to illuminate the bottom of the wound minimizing shadowing. While operating under surgical loops of 2.5 magnitudes, the disclosed headset with a larger field of view diameter is preferred. For surgery using 4.0 loops a headset that has a higher columniation beam with slightly higher intensity roughly 20% higher output provides 100% illumination with a 4× optical loop. Using an elliptical reflector to focus light. Due to the nature of the preferred HID lamp there are several control areas of concern, temperature, control and cooling, electromagnet contamination or conformity (EMC). Temperature control effects lifespan of the HID lamp as well as temperature color output, preferably in the range of 5000 to 6000 Degrees Kelvin but around 5500 Degrees Kelvin is desired. The elliptical reflector and ballast are contained in a semi-enclosing surrounding heat sink/light cable bracket with the HID lamp and reflector sealed to the upper heat sink maintaining stable temperature, and containing airflow providing repeatable light quality and life expectancy while shielding high frequency (EMI). Upper and downward are used in the sense that the portable headlight assembly is pointed down when affixed to the practitioner in use. a fixed CFM (cubic feet per minute) fan mounted in a formed cooling duct accomplishes cooling. EMC shielding directs airflow into and over the heat sink that is sized for cooling the HID lamp rated at 9-14 watt.

The heat sink has elongate grills composed of longitudinal fins with elongated ventilation openings to HID lamp and reflector temperature internally and externally. The HID lamp temperature is controlled by providing controlled heat dissipation through the thermally conductive surfaces of the heat sink and light cable bracket for maintaining the temperature surrounding the HID lamp in the range of 121 degrees C./250 degrees F. to 148 degrees C. to 300 degrees F. Excessive heat build up is transferred through the elongate ventilation openings to pass the air flow to conductive cooling channels between finned intake and exhaust grills located on the housing the outer surface, these grills interface with duct extensions located in the support belt allowing portable headlight assembly to be worn inside an environmental suit (spacesuit) or under surgical garment with the duct extensions exposed to free air. Functional safety concerns are addressed both electronically and dynamically. The HID lamp operation is controlled by the insertion of the light cable bracket into the portable headlight assembly causing HID lamp exercitation, to turn on, there by eliminating the possibility of the portable headlight assembly being misplaced with the HID lamp activated and no light cable blocking the HID lamp and possibly causing fire or chance of a burn to the practitioner, assistant or environs. a switch couple the power supply and ballast in the portable headlight assembly when the light cable is fully inserted into the light cable bracket; the switch can be mechanically changed, include a proximity sensor, i.e. hall effect inductive, etc.

The temperature control of the nickel halide bulb is critical to HID lamp life and control of desired color temperature of the illumination. at temperatures below 150 C the mercury vapor will burn off or attach to the walls causing a change in correlated color temperature and lifespan of HID lamp over time. Fluctuation in HID lamp temperature will cause flickering. The environment surrounding the HID lamp with the elliptical reflector for controlling heat dissipation primarily through the heat sink will not exposed the HID lamp to turbulent air and temperature change. The HID lamp with the elliptical reflector is assembled to fit within the heat sink. The ballast is just aft of the reflector and conjugates in thermal conductive relation with the heat sink. a wave washer between the ballast and a shoulder on the inner wall of the heat sink urges the ballast and the elliptical reflector together. For thermal conductivity and there is a thermal dielectric compound to transfer heat from the ballast to the heat sink with fins. The elongated vent maintains a constant lamp temperature by cooling the back of the elliptical reflector and that area is critically matched to the lamp, airflow heat sink surface area. a light cable bracket holds the reflector at the correct focal length to the F2 of the elliptical reflection and centers it while enclosing the HID lamp chamber and maintains constant temperature with its surrounding outside heat sink. The temperature about the HID lamp and reflector is regulated by cooling air flowing through calibrated elongate slots in the base of the light cable bracket. There may be an optional Hepa filter for medical cases with possible air borne exposure such as staph aureus bacteria or other contaminates. The system has a primary Hepa filter that can be positioned between the lamp module the support belt. That Hepa filter handles environmental contaminants by preventing their circulation by the cooling fan assembly. For example a patient may have bacterial infection so airborne contamination might result without the Hepa filter. Tests made without the require additional airflow cooling resulted in the ballast, HID lamp and reflector base initial temperature of 166 C in static ambient air the temperature and rapidly increased from that. The heat sink and light cable bracket also functions as an EMC/RF shield necessary due to the nature of arcing of the HID lamp. The 6 KVW starting surge and minimal run current are absorbed by the aluminum heat sink and light cable bracket receptacle so a high percentage of the EMC/RF.

The electronic safety during operation, charging and shipping is monitored by a controller board for regulating battery voltage, battery charging and discharge current, battery charging and discharge temperature, internal temperature of case, HID lamp, heat sink, and recording battery charge history including percent of charge, numbers of charges, battery capacity depletion overtime, adjustable calibration for battery power level display. The battery power level as percent of charge has a display including five light emitting diode groups. Each group has light emitting diodes of three colors green, yellow and red. Each of the five light emitting diode groups represents 20% of the battery charge. Change in color is broke down into 6% increments represented by changing color of each of five light emitting diode groups. a full charged battery would begin with all five light emitting diode groups glowing in the green state. This would represent a loss of 6% with 94% remaining, as the charge depletes the next or second group of light emitting diodes will change to yellow then to red showing an additional 6% loss with the total charge left at 88%. When the charge level drops to below 80% the first and second red light emitting diode groups of the five will shut off leaving the remaining light emitting diode groups in the green state restarting the sequence. 6% a total of 20% of charge for each light emitting diode groups.

Control of battery discharge, current and voltage is on an individual cell level. Each battery in the power supply has of four lithium ion cells. If programs are out of range output or charging is shut-off. Cooled temperature controller ballast and lamp system includes an electronic programmable system control board that monitors battery voltage, current and temperature of both batteries and lamp with safety limits. The ballast is in a plastic housing. The lamp has a plastic base with glass/Pyrex reflector. So if the operating temperature for battery, housing and HID lamp assembly has exceeded programmed limits during operation and is out of range the portable headlight assembly will be automatically shutoff. The board has two extending thermo couples TC1 and TC2 that have programmable limits so the maximum internal case temperature is read by TC1 and its limit is 140 F/60 C. The lamp assembly heat sink is read by TC2 projected through the cooling duct to the lamp assembly also set at 140 F/60 C. Similarly there are standards for cooling air transported around the lithium ion, polymer battery that is monitored by the board controller. Thus heat-sink temperatures, battery temperatures, system and individual cell current and voltage are maintained to predetermined limits and will for example, turn off charge cycles and set percent of charge used on the basis of the life history of the portable headlight assembly. The heat sink consists of ballast heat sink and light cable bracket that hold the ballast, HID lamp and reflector constructed of a thermally conductive material it is currently preferred to use an aluminum alloy. alternatively, any conductive material or composite, it could be substituted, e.g. a copper thermally conductive plastic, etc. Similarly, cooling tubes (not shown) as they are commonly used in notebook computers for transfer of heat via copper tubes filled with coolant transfer heat to the heat sink. Thus heat is transferred and absorbed for dissipation with just fins or fins and tubes. The highest heat build up is at the center of the reflector, the area is open to cooling air to eliminate excess heat build-up at the ballast so the upper left corner (outside reflector has openings for cooling relief. From the perspective of the portable headlight assembly is normally horizontal in its belt or holster holder and vertical when used in the charging station. The top of the reflector is sealed to the light cable bracket allowing cooling with the constant temperature while aligning the focal point of the reflector to the light cable. Thus, the fiber optic cable extends toward the practitioner's headset. To adapt for different surgical requirements, e.g., were a surgeon to operate without a surgical loop a larger diameter field of vision or spot diameter could be provided. The disclosed unit maintains high efficiency with matching the best efficient use of the disclosed fiber optic cable to lens assembly. Three different headsets, rather than using an adjustable focus for the aperture size gives the disclosed higher energy than normal output because of the designed specific lens focal length for each application for general surgery without loops or a surgeon with low magnification needing a 2.5 diameter inch spot whereas a neurosurgeon using high magnification 4× needing roughly 1.5 diameter inch spot at higher intensity. Thus a maximum efficiency of the disclosed light output is provided for each of those parameters.

The axial thermal expansion of the heat sink is controlled by a wave of washer below that forces the heat sink against the elliptical reflector. There is a thermal compound between the ballast and its' heat sink to mitigating thermal expansion of the dissimilar preferably aluminum for the heat sink and for the ballast. Operator assembles the fiber optic cable assembly by inserting multiple of optic fibers into a sheath to form the light cable and attaching that fiber optic cable assembly into the heat sink airflow directing portable headlight assembly at its distal end. a translucent red silicone shield on the disclosed fiber optic cable, gives light with a blue hue that is a combination of the correlated lamp temperature of the lamp output the diffused energy going through that translucent shield. The condition of the disclosed translucent red silicone cable in the off position it is red once energized it changes to a fuchsia, i.e., purplish pink. While this has been tested and found non-distracting in surgery it does provide the red control signal in the "FDA" requirements for surgical instruments. Lamp battery does not have an infinite power source, plugged into the wall, its a significant battery life of 4 hours so that once the lamp is turned off or there is a failure the cable returns to its red state signifying that it does require attention to swap out the battery pack. That is the lamp is off and requires attention. The battery can be switched within the 5 minute required FDA time limit. The conjugation of the proximal end of the cable assembly into the distal recess of the airflow directing portable headlight assembly activates the HID lamp assures safe operation and protects against burns and heat delivered to the practitioner, assistants and environs. The portable headlight assembly has a battery charge level indicator viewable on the front face of the portable headlight assembly. Connecting the portable head light assembly by placing it on charging station connects the batteries to rectified line current transformed to the proper charging voltage to recharge. The display of power level status light emitting diode groups as explained indicates the amount of battery charge remaining. The housing is "ABS" plastic material molded ergonomically with a no slip finish and includes internal structure to safely and reliably support the portable headlight assembly components while meeting UL/CE test standards requirements. The portable headlight meet all the FDA and UL requirements for maximum infrared or ultraviolet output per square centimeter and is well within those ranges with very low to no heat output on the patient from the lens. The system configuration to match requirements for surgical illumination requires that the surgical lamp be replaced within 5 minutes at any given point of a procedure. To match this requirement a double charging station or a quadruple charging station can be used. These units are independent and any number of them depending on the length of the surgery. Each lamp module will run for up to 4.5 hours so depending on the length of time needed they can pull as many modules as necessary.

The portable headlight assembly is compact for use by the practitioner to examine anatomical structure includes preferably a HID lamp made to meet the color temperature requirements at the operating temperatures disclosed herein by Lighting Products Division at 4619 Jordan Road, Skaneateles Falls, N.Y., 13153. That is a high intensity metal halide in this disclosure referred to as, HID lamp, and it is wherefrom illumination is emitted by an arc discharge between two closely spaced electrodes hermetically sealed inside a small quartz glass tubular envelope. The preferred lamp is a model ED 401 coupled directly to G2 ballast set up for 14 watt and supplied with 12 volts DC input. The ED 401 lamp has a reflector that is elliptical in cross section carrying the lamp at its base and flanged about its mouth. The elliptical reflector has to focal points one in the arc and another at the plane of a multi strand fiber optic bundle. The illumination emitted from that arc lamp is intense and appropriate safety precautions relating to exposure protection are required. Metal halide lamps operate at very high temperatures and pressures so the quartz glass must be kept clean and the glass lamps should be handled with care giving special attention of the quartz arc tube.

DETAILED DESCRIPTION

The following description is specific to a preferred working embodiment at the time of filing this disclosure. Proper mounting, cooling, and ventilation are required to assure reliable operation of metal halide lamps. Metal halide lamps use high voltage, short duration pulses to initiate operation. The HID lamp wired with proper electrical polarity to prevent damage to the lamp. Ballast products are electrostatic sensitive electronic assemblies and should be so handled. Proper Electro-Static Discharge (ESD) handling procedures must be employed. The preferred mounting includes a finned aluminum tube with vents. The tube bears against the backside of the elliptical reflector flange and is resiliently biased by a wave washer that pushes the finned aluminum tube toward the fiber optic bundle plane. Shims in the form of thin washer(s) may be added against the front side of the flange to space the focal point of the arc of the HID lamp precisely at the fiber optic bundle plane. The HID lamp is the preferred configuration used with a small elliptical reflector.

A fan is disposed centered within the finned aluminum tube and coaxially forward of the G 2 ballast to provide air flow against the back of the elliptical reflector thereby regulating the lamp temperature and maintaining the color temperature of the illumination emitted to preferably 5500 Degrees Kelvin. The fan, the finned aluminum tube, the HID lamp are along and aligned with the axis so they form a compact assembly running at relatively low wattage. The power supply is included within the housing to energize the HID lamp and fan for up to 4 to 5 hours of use.

Cooling is required to ensure proper HID lamp arc during operation and acceptable life, appropriate forced air-cooling must be provided when enclosed within the housing. Cooling must be sufficient to maintain the temperature at the tip of the arc tube between 200° C. and 285° C. Care must also be taken not to overcool the HID lamp. The fan is a position fit coaxially within the cooling duct formed within a hollow of the finned aluminum tube. This will result a consistent arc that is bluer in color but may cause some flicker. The ballast is cylindrical and resides in a well-ventilated finned aluminum tube held by the housing. Forced air-cooling is needed in the housing, but is not a strict requirement.

A Q401 FET heat sink (largest heat sink on PC board) located adjacent to the input power connections must be maintained below 90° C. and the aforesaid air-cooling assures that as needed. For an optimum temperature measurement location a thermocouple adheres on the reverse side of the Q401 heat sink at the same height as the FET.

Mounting the HID lamp is specified and engineered for operation in a set orientation, such as horizontal or vertical base down. To prevent damage during HID lamp installation, mounting, and replacements, care must be taken to avoid mechanical interference with the quartz arc glass. Mount the ballast as described by at each of the four corners via provided through holes. although it can be affixed to the circuit board assembly or some other acceptable means that is not preferred as it is in line with and along the axis of the HID lamp and fan. Handling and mounting care should be exercised to prevent mechanical stressing of components on the through hole side of this assembly. The ballast provides a series of high voltage pulses during lamp starting. To avoid electric shock and arcing appropriate isolation techniques of equipment directly adjacent to the lamp and ballast. For example, under normal relative humidity conditions, an air gap of 9.53 mm (0.375") is recommended if there is no additional isolation used.

The gas discharge lamp achieved the highest circadian effect coefficient, followed closely by the halogen light with high color temperature. By comparison, the surgical light with low color temperature showed a poorer performance, achieving a circadian effect coefficient approximately 25% below that of the halogen light with high color temperature. Dimming the three lights during operation gives a different outcome. The only lamp to maintain its high stimulating effect when operated at reduced luminance is the gas discharge lamp with opto-mechanical dimming. By contrast, electronic dimming of the halogen lights results in an altered color spectrum, impairing the physiological effect of the other two lights.

The HID lamp is connected with a standard two-prong connector, commonly known as an AMCI connector. Thus, the AMCI connector from the power supply. The fiber optic cable of multiple optic fiber strands preferably and for substantially uniform illumination of the surgical site the fiber optic bundle has in the range of 3000 to 10000 fibers. The fiber optic cable of multiple optic fibers is also a color filter to assure the desired color temperature of 5000 to 6700 degrees Kelvin. The fiber optic cable has at its end away from the portable headlight assembly an optic selected to provide substantially uniform illumination of about 32,000 LUX at a focal distance of about seventeen inches or twenty three centimeters of about twenty seven candle power over a preferred focal diameter of approximately, two and one half inches or six point one centimeters. a double convex primary lens followed by a first surface mirror and finally focused by achromatic lens system base on lighting and focal working diameter. The collimation of the illumination at the end away from the portable headlight assembly is preferably enhanced by the double convex lens disperse any mottled pattern and provide a uniform collimated dispersion of illumination at the surgical site. The preferred illumination may be uniform over a circle in the range of 2.5 centimeters to 10 centimeters diameter. The correlated color temperature is optimized between 5500-6700 Degrees Kelvin depending on the application. The CRI (color rendering index) of the disclosed system is greater than 80 and may be as much as 94. CRI is a measure of the light quality of a light source as compared with sunlight (which is given the maximum CRI value of 100). The closer a light source's CRI is to 100, the better its ability to show true color. The actual lamp output is different than the onsite load due to the lens fiber optic cable configuration the overall design causing the onsite to meet all the FDA and UL certifications by requiring a min of UV and IR output and also an optimum correlated color temperature and CRI.

The preferred power supply is a rechargeable lithium ion battery pack mounted in the housing to provide a compact rechargeable supply of direct current to the fan and the lamp. The battery technology hinges on the development of safe, reliable and advanced lithium-ion batteries for hybrid and plug-in technology from automotive companies. Nissan, for example, are said to have a laminate battery configuration which is more compact and thus in the same volume more energy dense. Because of the great search for more watt density the future would appear to hold much in the expected development of greater watt density per unit volume and/or weight. The GM volt vehicle plan is to use a new generation of lithium-ion batteries, which are reported to have greater energy capacities. In order to generate a steady supply of these batteries, the U.S. Advanced Battery Consortium has awarded an $8.2 million contract to the Johnson Controls-Saft joint venture to develop the batteries, according to *Automotive News*. The Advanced Battery Consortium is part of the U.S. Council for Automotive Research, which is composed of many leading auto manufacturers looking to release lithium-ion batteries for their next-generation hybrids and electric vehicles, such as Ford, GM and Chrysler.

This disclosure therefore seeks to include battery development. a recharging dock or place to receive the input of line current at sufficient voltage and current to recharge the lithium ion batteries in a time frame that best suits the needs of the users and maximizes the life of the batteries is provided. Such technology is well known and is coupled by connectors or by an inductive coupling as preferred. In regard to the later there appears to be another development Massachusetts Institute of Technology researchers and Intel Corporation recently showed how to make a 60-watt light incandescent bulb glow from an energy source 3 feet away. It was done with 75% efficiency; this could recharge wirelessly a laptop computer or cell phone without plugging them into a charger. Wireless transmission of electricity uses electric coils that resonate at the same frequency transmitting energy to each other at a distance. Before that becomes a commercial product the distance, amount of energy and size of coils must be practical. Figuring out how to prevent the electromagnetic field from interfering with the device or medical environment could also be a problem as is loss of energy in transit. The best achievement has been 90% efficiency when the devices were 3 feet apart. With the low wattage on the order of less than 20 watts of the presently disclosed apparatus it might be feasible to have a transmitting coil positioned near the housing and a receiving coil in the housing such that during use the battery charge would be maintained thus reducing or elimination the required time on the charger. More importantly, that approach might be able to increase the time of usage without recharge beyond the four to five hours currently available. The disclosed battery powered surgical headlight has a 4.5 hr battery life approx 900 hours of total battery life depending on charge time cycles and abuse. The disclosed battery powered surgical headlight on the lamp assembly case includes a battery charge indicator. The indicator uses a programmable sensor that monitor cell voltage and cell current history of charge levels. The disclosed charger communicates charger the current rate of current draw for each battery each cell within the battery to determine if the correct current and voltage level are available. The charger can then brings the cells up to the correct value. On the output side of the LED's are 5 LED's each representing 20% of the correct total battery charge. Each LED represents 20% of the total charge. The LEDS show 3 colors, all five of them initially green as the battery lowers to below 90% of the charge the $1^{st}$ LED will change to yellow after it reduces to 80% sequencing down to the $2^{nd}$, $3^{rd}$, $4^{th}$ and $5^{th}$ LED which becomes red and the headlight shuts off. after the $1^{st}$ LED is red the $2^{nd}$ LED will pick up at green go to yellow then red and all the way down the line until all cells are drained. There is no minimum requirement for time; batteries do not require memory they can be plugged in. If the pack was to be ½ full it would be approx 2 hrs of charge at that point it may be used with no damage to the battery.

Alternatively, with the ongoing development of batteries it may even make the power supply cheap, small and lightweight enough to be a leapfrog technology in terms of portability. Fuel cells would provide identical advantages if price, weight and size came down. Those power supplies for the portable headlight assembly might be truly another step beyond the several hundreds of watts of power surgical fixed overhead surgical medical lamps currently available and used.

With reference to the drawings attached hereto as FIGS. 1 to 9 and the reference numbers therein the following description pertains. A portable headlight assembly 10 illuminates a surgical site for viewing by a practitioner 11 see FIGS. 1, 2 and 3. The portable headlight assembly 10 has a compact lightweight HID lamp 12 in FIG. 6 and a power supply 13 in FIG. 7 carried in a housing 14 see FIGS. 2, 3, 4 and 6. The portable headlight assembly 10 attaches to a wall outlet via a male plug shown schematically at 15 in FIG. 7 when not in use and only when battery recharging thus easy movement by or with the practitioner 11 is allowed. The HID lamp 12 has a fiber optic cable 16 extends there from to a head mounted double convex columniation lens 17 as in FIG. 9 to form a headlight source 18 in FIG. 2 supplying illumination from the HID lamp 12 that is operative only in a state wherein the light energy is directed via the fiber optic cable 16 toward the surgical site. The housing 14 encloses and surrounds the HID lamp 12 for safe handling and support within the housing 14 during movement with the practitioner 11. For illumination the HID lamp 12 is mounted within the housing 14 along an axis "A" shown in FIG. 6 for lighting the surgical site with approximately daylight at between 5000 and 6700 degrees Kelvin in FIGS. 5 and 6. The double convex columniation lens 17 in FIG. 9 act to substantially maintain the cross section of the aperture of the double convex columniation lens 17 by inhibiting the spread of the illumination after leaving the double convex columniation lens 17 and before reflecting off a first surface mirror 17' to redirects the illumination ninety degrees for passing through the achromatic magnifying lenses 17" with a fixed focal length consisting of a pair of bonded dissimilar glass lenses 17''' and 17'''' shown in the partial cross section of FIG. 9. The achromatic magnifying lenses 17" substantially reduces color separation of the redirected illumination to deliver a spot of light thus produce a uniform coloration at the surgical site.

Figure 5:
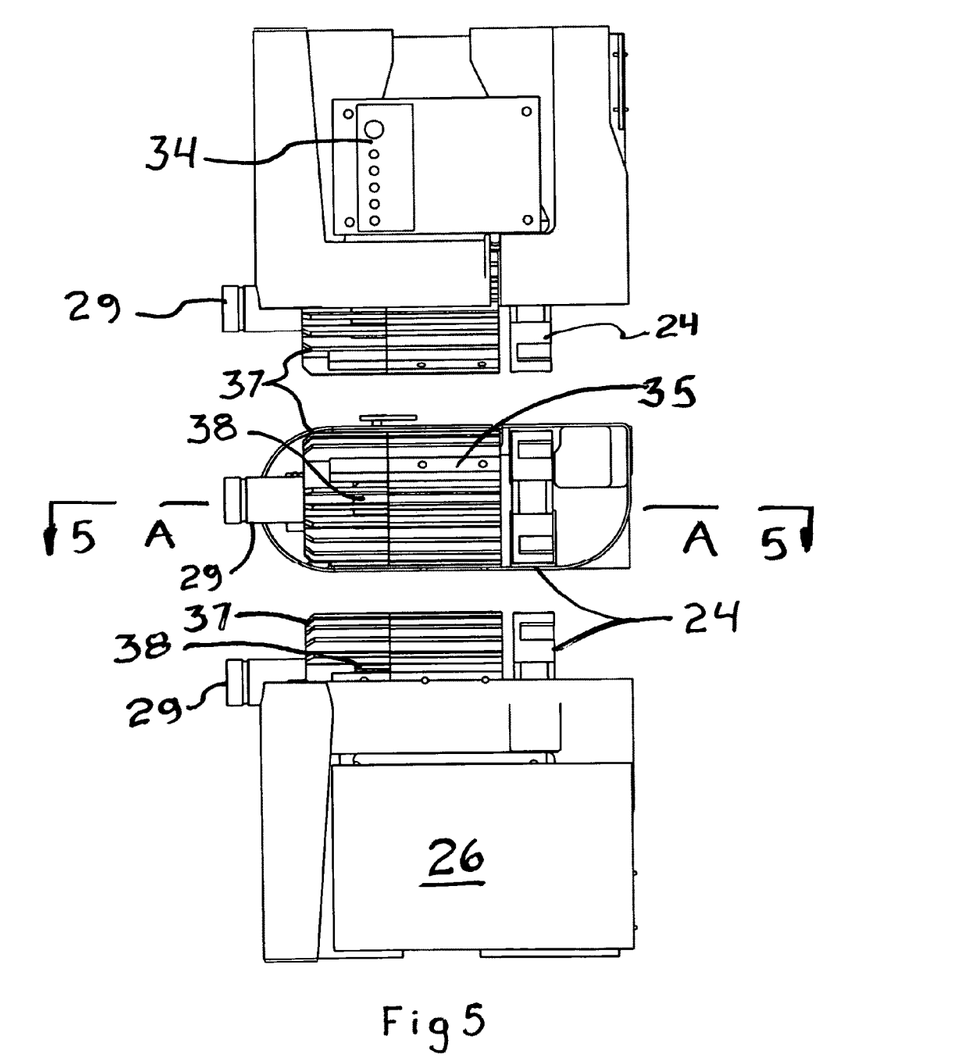
FIG. 5 is a front, back and side views of the portable headlight assembly the headlight source, including the heat sink and light cable bracket shown with the housing removed with the ballast, fan, elliptical reflector and HID lamp therein positioned.
Figure 6:
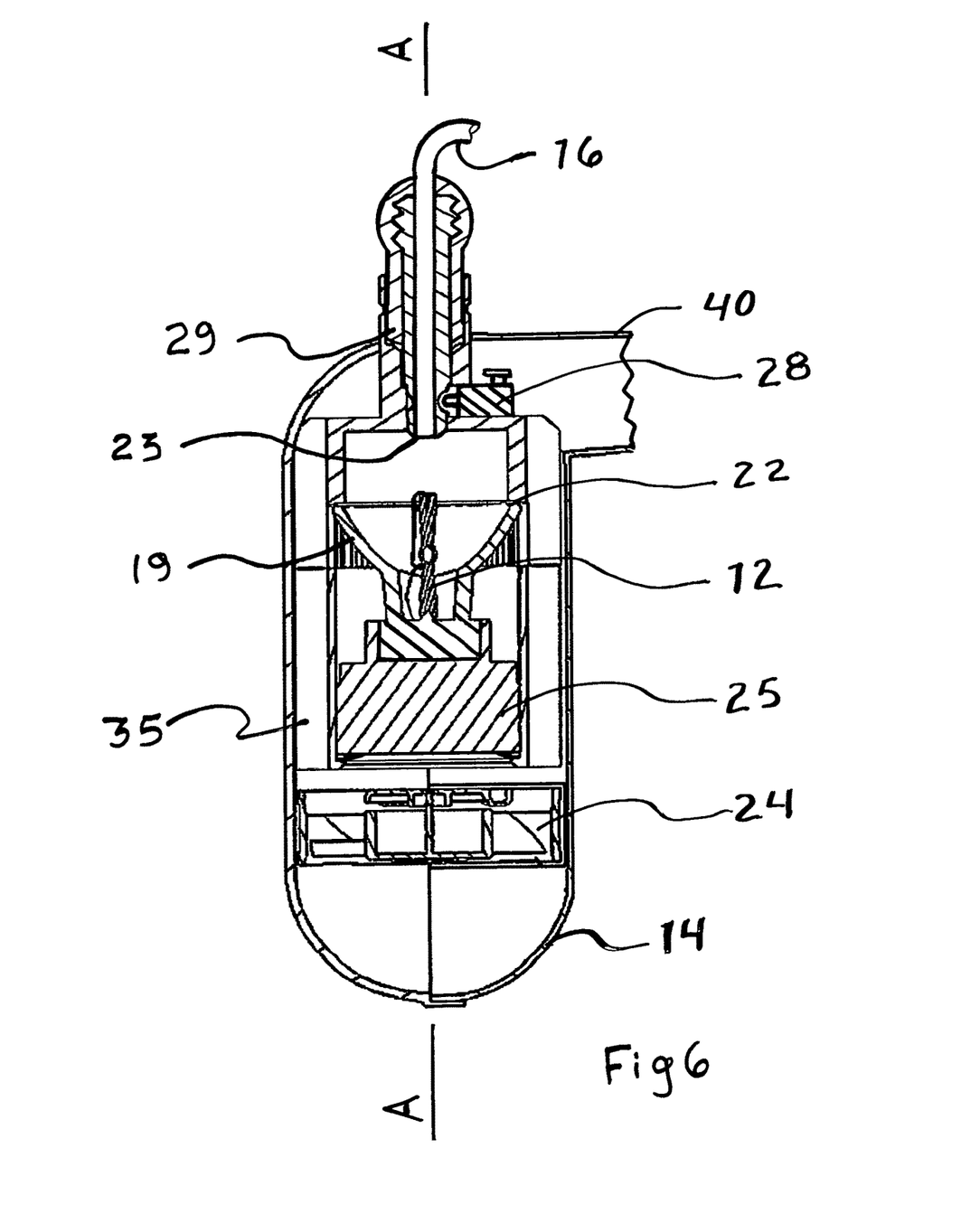
FIG. 6 is a view in cross section as seen along line 6-6 of FIG. 3 showing the fan, the ballast, elliptical reflector and HID lamp shown as they appear axial relationship to one another surrounded by the heat sink and the fiber optic cable engaged fully within the light cable bracket to close the switch and power the HID lamp.
Figure 7:
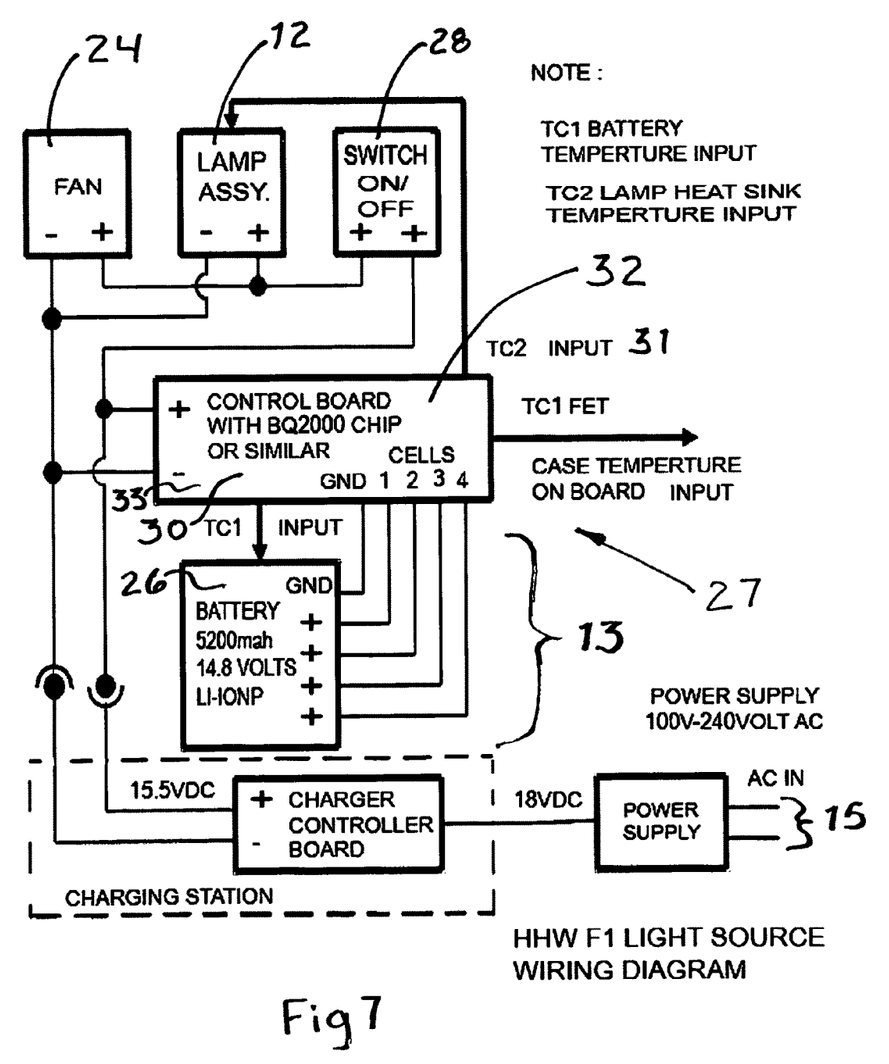
FIG. 7 is a schematic block diagram of the control circuit for the portable headlight assembly of the present disclosure illustrating the electrical connections, components and their operative relationships.
Figure 8:
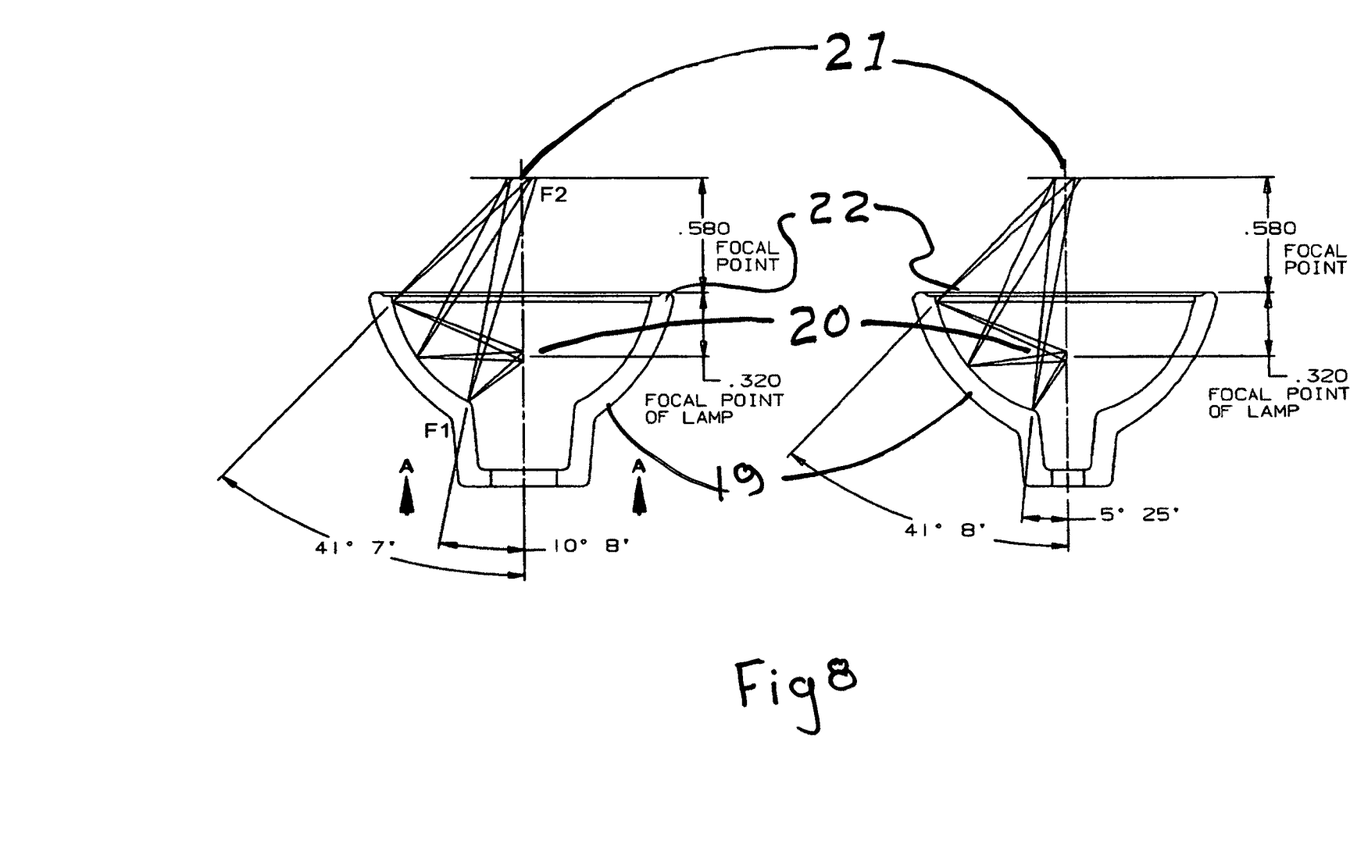
FIG. 8 is a pair of optical ray diagrams illustrating the elliptical reflector geometry and reflections and foci from the long side and the short side of the ellipse. Those schematic views are as if seen along cut line 5-5 in FIG. 5 and cut line 6-6 as shown in FIG. 6.

An elliptical reflector 19 in FIGS. 6 and 8 shown as a ray diagram about the HID lamp 12 is position with its near foci 20 at the arc within the HID lamp 12 and the far foci 21 at an open end 22 of the elliptical reflector 19 covered by a proximal plane 23 in FIG. 6 of the fiber optic cable 16. The elliptical reflector 19 supports, reflects and focuses the HID lamp 12 in position to radiate energy towards the surgical site. A fan 24 is located in FIGS. 5, 6 and 7 on the axis "A" upstream of the elliptical reflector 19 about a ballast 25 in FIG. 6 for the HID lamp 12 to move ambient air from outside the housing 14 there through and in convective communication with the elliptical reflector 19 for supplying cooling air flow against, about, around and over the elliptical reflector 19 for maintaining the HID lamp 12, the ballast 25, the elliptical reflector 19 and housing 14 temperatures at preferred limits.

A power supply 13 has a battery 26 in FIGS. 5 and 7 with individual cells connected in a control circuit 27 in FIG. 7 mounted within the housing 14 selectively coupled to the HID lamp 12 via a switch 28 in FIG. 6 adjacent open end 22 of the elliptical reflector 19 the proximal plane 23 of the fiber optic cable 16 completes the control circuit 27 sending light energy through the fiber optic light cable 16. A light cable bracket 29 in FIGS. 5 and 6 positioned near open end 22 aligns the fiber optic cable 16 along axis "A" when the proximal plane 23 is at the open end 22 and fully seated therein to close switch 28 and thus safely energize the HID lamp 12. Temperature responsive sensors 30 and 31 in FIG. 7 connect into the control circuit 27 and are located in the housing 14 near the battery 26 of the portable power supply 13 and the elliptical reflector 19 to monitor the HID lamp 12, respectively. A control 32 in FIG. 7 and control circuit 27 monitors the operation of the HID lamp 12 of headlight source 18 via temperature response sensor 30 for battery 26 of the portable power supply 13. The control 32 is reactive to the temperature responsive sensor 31 of the HID lamp 12 to activate and deactivate the coupling there between responsive to the radiation supplying illumination of a surgical site. The portable power supply 13 has battery 26 with cells monitored and regulated by the control 32 in accord with temperatures and individual cell current and voltage for holding each to a predetermined recharge limit by turning on or off charge cycles as required for each. A memory 33 within the control 32 records the life history of percent of charge used. A display 34 in FIGS. 2, 3, 4 and 5 visible from outside the housing 14 connects to the control 32 to show percent of cell charge remaining. The headlight source 18 includes HID lamp 12 and ballast 25 for supplying illumination between 5000 and 6700 degrees Kelvin; the ballast 25 is positioned against the elliptical reflector 19 for receiving the convective communication from upstream of the elliptical reflector 19. The ballast 25 couples to the HID lamp 12 to energize the HID lamp 12. The fan 24 the ballast 25, the elliptical reflector 19, and the HID lamp 12 are disposed in line along axis "A".

A thermally conductive heat sink 35 in FIGS. 5 and 6 supports and surrounds along axis "A" the fan 24 the ballast 25, the elliptical reflector 19, and the HID lamp 12 within the housing 14 for directing the convective communication there about and there through and for also conductively ameliorating the temperature difference between the ambient temperature outside the housing 14 and the heat generated by the HID lamp 12, the ballast 25 and the fan 24. The conductive heat sink 35 is located adjacent the housing 14 exhaust grills 36 in FIG. 4 access of the conductive heat sink 35. In particular, there are in heat sink 35 fins 37 with elongate ventilation openings 38 shown in FIG. 5; the fins 37 and ventilation openings control HID lamp 12 and elliptical reflector 19 temperature internally and externally. Fan 24 drives airflow through the housing 14 a vent for air flow in 39 in FIG. 4, about conductive heat sink 35, over fins 37 then passing through elongate ventilation openings 38, by ballast 25, to light cable bracket 29 and elliptical reflector 19 and out of housing 14 through exit vent 40 for air flow out in FIG. 4. Heat build up is transferred on intake and exhaust grills 36 located on the housing 14 the outer surface there through to conductively cool the channels between fins 37 and past the elongate ventilation openings 38 to the elliptical reflector 19. These grills 36 interface with duct extensions not shown but located in the support belt 41 in FIG. 1 allowing portable headlight assembly 10 to be worn inside an environmental suit (spacesuit) or under surgical garment 42 also in FIG. 1 with the duct extensions exposed to ambient air. The support belt 41 acts as flexible ducts connecting to vents 39 and 40 connect to pass ambient air into and exhaust hot air out of the housing 14.

Figure 1:
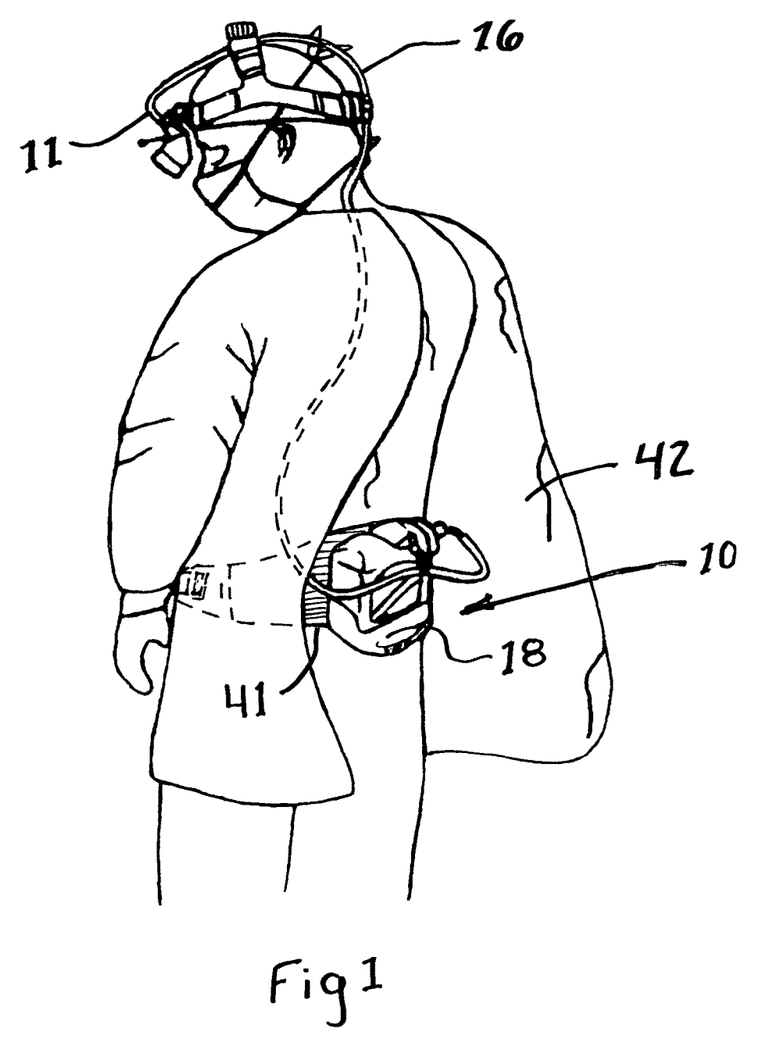
FIG. 1 is a perspective view as seen from in back of the practitioner showing the portable headlight assembly positioned on the practitioner by a belt with the fiber optic cable extending to a head strap positioning the lens toward the surgery for maintaining the desired color temperature illumination of a surgical site to clearly define anatomical structures.
Figure 2:
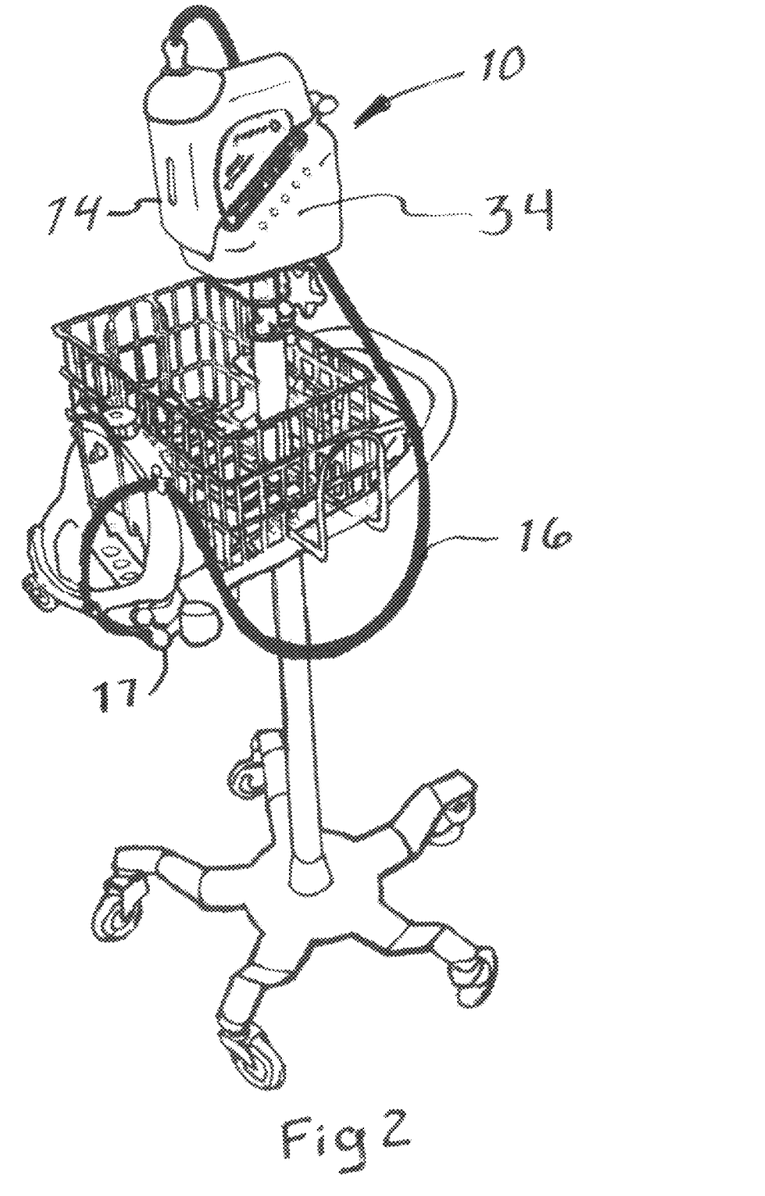
FIG. 2 is a perspective view of the practitioner with the portable headlight assembly supported on and movable with a pole on casters; the practitioner would wear the head strap and lens while the pole remains nearby.
Figure 3:
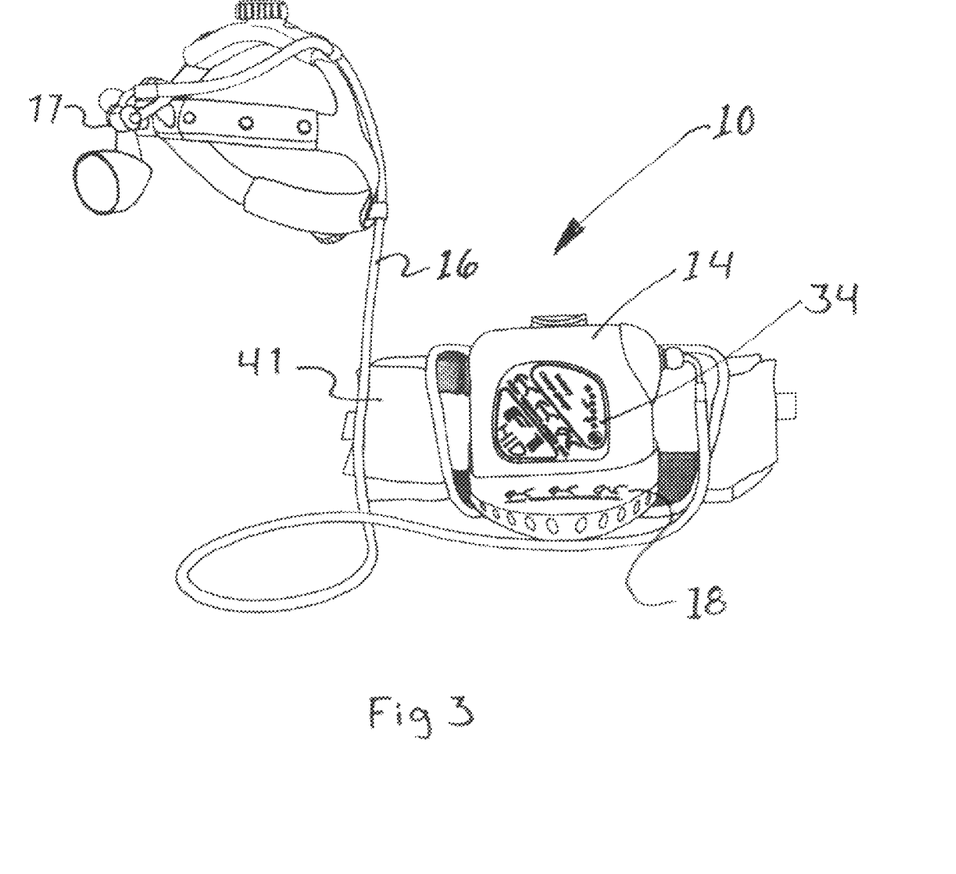
FIG. 3 is a perspective of the portable headlight assembly showing the head strap and headlight source connected by the fiber optic cable.
Figure 4:
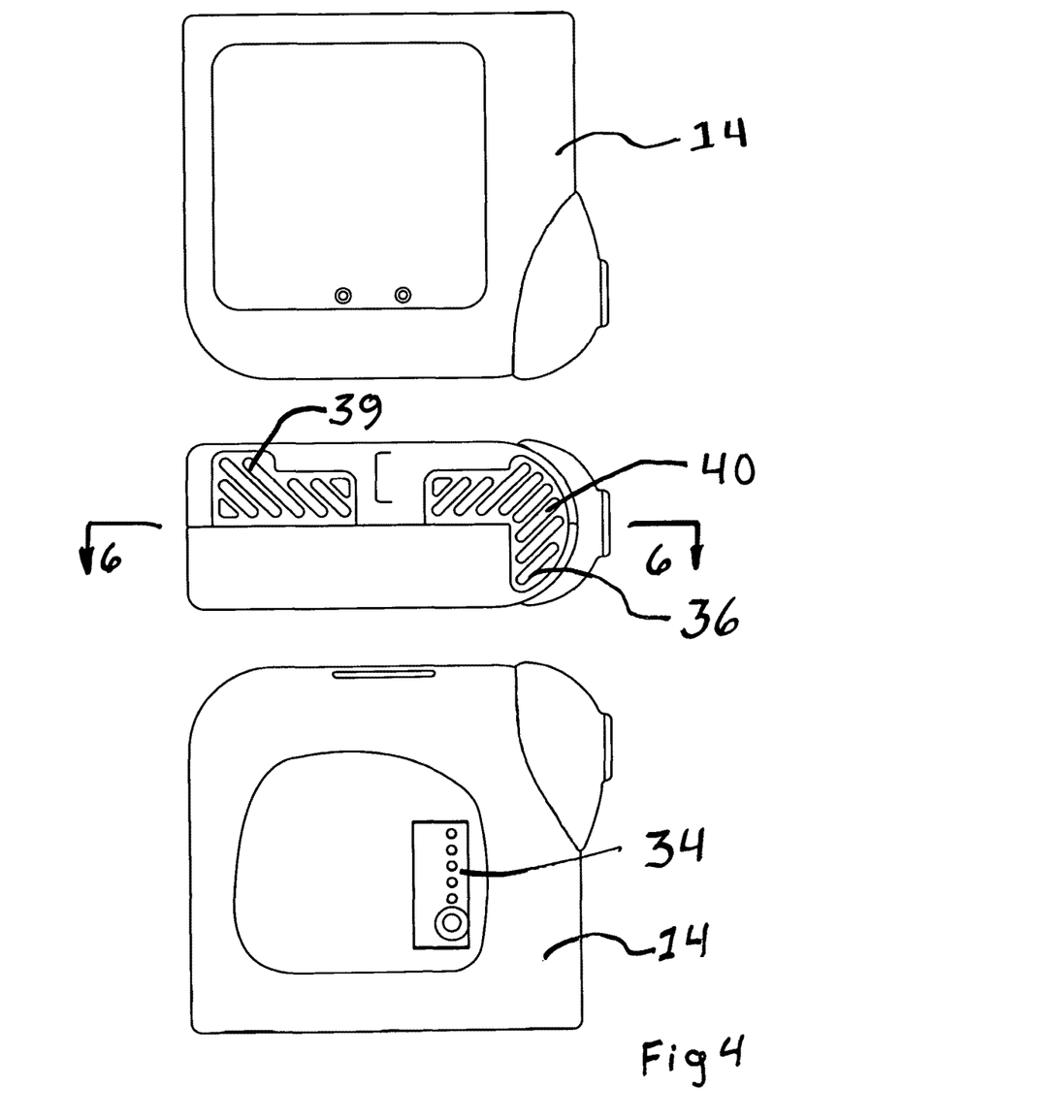
FIG. 4 is a front, back and side views of the housing of the portable headlight assembly.
Figure 9:
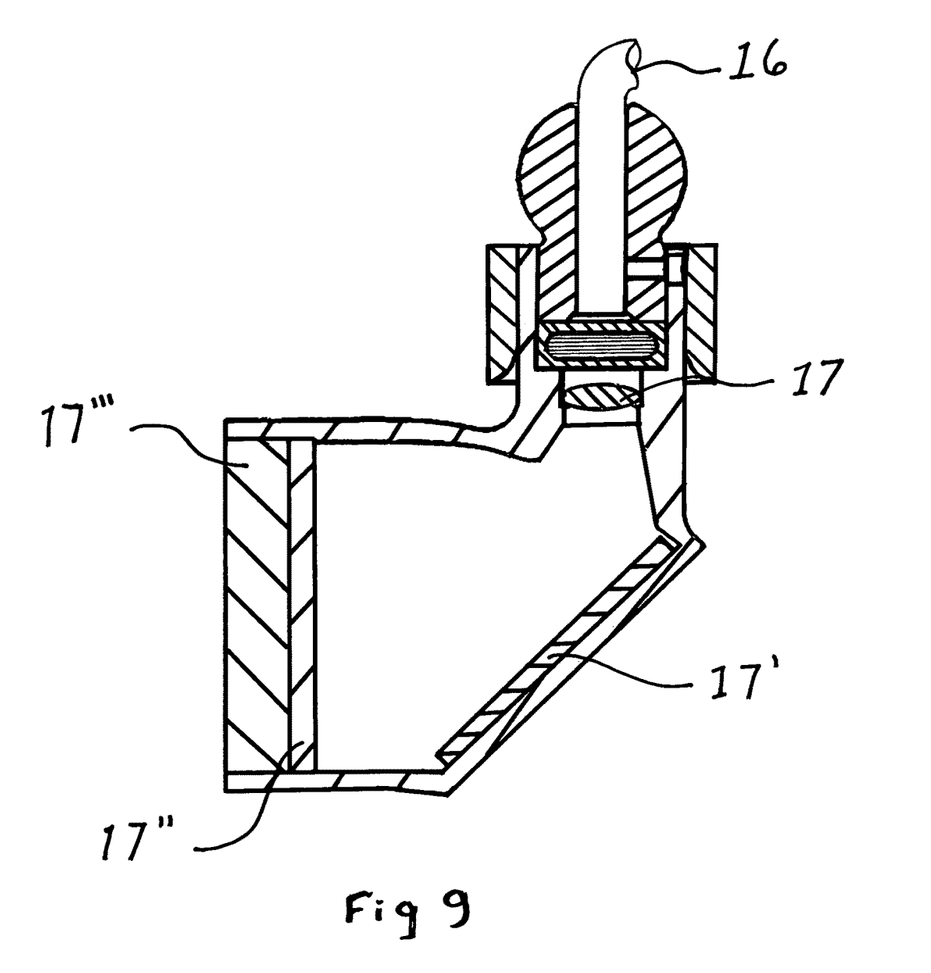
FIG. 9 is a perspective view of the lens for the HID lamp at the far end of the fiber optic cable carried on the head strap, the double convex columniation lens before a mirror to redirects the illumination ninety degrees then passing through an achromatic magnifying lenses with a fixed focal length consisting of a pair of bonded dissimilar glass lenses shown in partial cross section.

The light cable bracket 29 is positioned near the elliptical reflector 19 open end 22 to align the fiber optic cable 16 of multiple optical fibers so the fiber optic cable 16 with its proximal plane 23 thereof to receive the focused illumination from the HID lamp 12. The light cable bracket 29 thermally interacts with the elliptical light reflector and the heat sink 35 to transfer heat and maintain the constant temperature of the headlight source 18 particularly the elliptical reflector 19. The fiber optic cable 16 extends as shown in FIG. 1 to double convex columniation lens 17 for transmitting illumination from the HID lamp 12 and elliptical reflector 19 to the surgical site as shown in FIG. 9. The shape of elliptical reflector 19 collects the light from the arc of HID lamp 12 at elliptical reflector 19 near foci 20 and transmits and focuses that light at far foci 21 schematically shown in FIG. 8 where the elliptical reflector is shown in cross section illustrating the locations of the near foci 20 at the arc of HID lamp 12 and the far foci 21 at the open end 22. FIG. 8 has two schematic views as if seen along cut lines 5-5 in FIG. 5 and cut lines 6-6 as shown in FIG. 6.

When the far foci 21 and the proximal plane 23 of the fiber optic cable 16 are the same distance from the arc of HID lamp because the fiber optic cable 16 is fully seated in light cable bracket 29 and switch 28 closed HID lamp 12 will illuminate. That safety feature is the result of the position of the proximal plane 23 at the open end 22 by seating of fiber optic cable 16 upon insertion into the light cable bracket 29 and at the same time engaging and closing switch 28 coupled into control circuit 27 in FIG. 7 with the portable power supply 13 and to energize the HID lamp 12, the ballast 25 and the fan 24. Thereby the HID lamp 12 will only illuminate safely when the fiber optic cable 16 is fully seated in conjugate position with the proximal plane 23 located at the far foci 21 of the elliptical reflector 19. The control 32 is located on a printed circuit board in FIG. 7. These components are in the housing 14 proximate the portable power supply 13, the ballast 25 and the fan 24 in position within the housing 14 up stream of the fan 24 adjacent the elliptical reflector 19 so the temperature responsive sensors 30 and 31 are location is in thermal contact with the battery 26 of portable power supply 13 and the elliptical reflector 19 to monitor the headlight source 18 temperature, the operation of the HID lamp 12, respectively. The double convex columniation lens 17 in FIG. 9 act to substantially maintain the cross section of the aperture of the double convex columniation lens 17 by inhibiting the spread of the illumination after leaving the double convex columniation lens 17 and before reflecting off a first surface mirror 17' to redirects the illumination ninety degrees for passing through the achromatic magnifying lenses 17" with a fixed focal length consisting of a pair of bonded dissimilar glass lenses 17''' and 17'''' shown in the partial cross section of FIG. 9. The achromatic magnifying lenses 17" substantially reduces color separation of the redirected illumination to deliver a spot of light thus produce a uniform coloration at the surgical site.

The claims that follow seek to cover the structures and method steps allowing mobility, safety and illumination of a surgical site for a practicing doctor observation with daylight during surgery. The portable headlight assembly 10 includes an efficient, compact, light in weight portable structure for illuminating a surgical site when look at by a surgeon safely operative only when the light energy is directed toward the surgical site. While the portable headlight assembly 10 disclosed in the detailed description and figures is specific it should be understood that skilled artisans will be able to substitute alternate power supplies, lamps, controls, structures for support, mounting, air flow paths and operation without departing structures and methods sought to be protected. Although the invention herein has been described with reference to particular specific embodiments, it is to be understood that these embodiments are merely illustrative of the principles and applications of the present invention. It is therefore to be understood that numerous modifications such as different HID lamps, ballasts and batteries and chargers may be made to the illustrative embodiments and that other arrangements may be devised to the housing, components, controls, circuitry, etc. without departing from the spirit and scope of the present invention as defined by the appended claims.

The invention claimed is:

1. A rechargeable portable headlight assembly for illuminating a surgical site for viewing by a practitioner, the portable headlight assembly for movement by or with the practitioner, the portable headlight connectable to a charger when connected to line power for recharging and the portable headlight assembly operative only in a state wherein the light energy is directed toward the surgical site comprising:
   a headlight source including a headlight lamp, a reflector with a headlight lamp end and an open end to reflect and focus an illumination and for directing and delivering radiant energy towards the surgical site, the headlight lamp and reflector mounted along an axis for supplying illumination between 5000 and 6700 degrees Kelvin;
   a housing to enclose and surround the headlight source for safe handling and support for movement with the practitioner, the housing including vent grills in and out thereof;
   a fan positioned coaxially along the axis within the housing in convective communication for supplying cooling air flow against, about, around and over the reflector and through the headlight source, the fan located in the housing for drawing ambient cooling air through the vent grills into and out of the housing;
   a heat sink mounting and supporting the headlight source along the axis within the housing about the fan and the reflector to guide air flow during a convective communication there through;
   a portable power supply coupled to the headlight source when the light energy is directed towards the surgical site, the portable power supply rechargeable when connected to the charger;
   temperature responsive sensors to monitor temperatures of the headlight source and portable power supply; and
   a control for monitoring the operation of the headlight source and the portable power supply, the control reactive to the temperatures of the headlight source and the portable power supply to activate and deactivate the coupling there between, the control responsive to a level of energy in the portable power supply and electromagnetic radiation at least when supplying illumination of the surgical site.

2. The portable headlight assembly of claim 1 wherein the control has battery cells monitored and regulated by the control in accord with temperatures and individual cell current and voltage for holding each to a predetermined recharge limit by turning on or off recharge cycles; and a memory within the control for recording life history of percent of charge used.

3. The portable headlight assembly of claim 2 wherein a display is connected to the control to show percent of charge remaining.

4. The portable headlight assembly of claim 1 wherein the headlight lamp is a HID lamp for supplying illumination between 5000 and 6700 degrees Kelvin, and wherein a ballast is positioned along the axis against the reflector and coupled to the HID lamp for receiving the convective communication before the reflector, the ballast coupled to the HID lamp to energize the HID lamp; the fan, the ballast, the reflector, and the HID lamp surrounded by and coaxial within a central passage of the heat sink that carries there in and there along on the axis the HID lamp, the ballast, the reflector, the fan, within the housing, the heat sink includes fins radially thereon and elongate openings there through to receive ambient air drawn through the housing vent grills and conveyed to the central passage for directing the convective communication there about and there through ameliorating the temperature difference between the ambient air and the heat of the HID lamp, the reflector, the ballast and the fan.

5. The portable headlight assembly of claim 4 wherein a light cable bracket positioned about the heat sink down stream of the reflector aligns along the axis so a light cable having multiple optical fibers has a proximal plane thereof to receive the illumination from the HID lamp to transmit illumination from the HID lamp and reflector, via the light cable, to a lens carried on a head strap worn by the practitioner for delivering the illumination towards the surgical site.

6. The portable headlight assembly of claim 5 wherein the reflector is elliptical in shape to focus the light from the HID lamp at a near focal point of the reflector at a far focal point near the open end of the reflector for receipt at the proximal plane of the light cable when positioned near the far focal point to illuminate the proximal plane.

7. The portable headlight assembly of claim 6 wherein the light cable upon insertion into the light cable bracket engages and closes a switch mounted there within and coupled in circuit with the portable power supply to the switch and energize the HID lamp, the ballast and the fan so that the HID lamp will only illuminate safely when the light cable seats in conjugate position substantially at the proximal plane located near the far focal point of the reflector after seating conjugation of the light cable into the light cable bracket.

8. The portable headlight assembly of claim 6 wherein the control for monitoring the operation of the headlight source and the portable power supply is a printed circuit in the housing near the portable power supply, the ballast, and the fan, in convective communication with air flow of the fan and adjacent the reflector, the printed circuit board including temperature responsive sensors located in at least in thermal communication to monitor and control several headlight source temperatures.

9. A portable headlight assembly for illuminating a surgical site when looked at by a surgeon, the portable headlight assembly for movement by or with the surgeon and operative only in a state wherein the light energy is directed toward the surgical site, the headlight assembly comprising:
   a. a headlight source including a HID lamp capable of supplying illumination at the surgical site via a light cable coupled to receive and transmit the illumination in the range of natural daylight between 5000 and 6700 degrees Kelvin;
   b. a portable power supply of less than 40 watts coupled to the high intensity discharge lamp when the light cable is located to receive focused light from the HID lamp;
   c. a control for monitoring the operation of the headlight source and the portable power supply, the control responsive to temperatures of the headlight source and the portable power supply, the control responsive to the level of energy in the portable power supply, and radiation supplying illumination, and
   d. a multi fiber optic bundle in the light cable extending from the HID lamp and guiding illumination from the HID lamp and the reflector to a lens carried on a head strap worn by the practitioner for delivering the illumination towards the surgical site to aim the illumination toward the surgical site, wherein the multi fiber optic bundle includes several thousand fibers sufficient to transmit and illuminate the surgical site for enhancing the color spectra of the visual field during surgery for providing the surgeon improved clarity in observation including depth of field and natural colorations during surgery.

10. A method of safely using portable headlight assembly for illuminating a surgical site when looked at by a surgeon including the following steps:
    a. positioning the portable headlight assembly for movement by or with the surgeon;
    b. supplying illumination at the surgical site with a headlight source including a HID lamp capable, via a light cable when coupled, to receive and transmit the illumination in the range of natural daylight between 5000 and 6700 degrees Kelvin;
    c. energizing with a portable power supply coupled to the HID lamp when a light cable is located to received focused light from the HID lamp for operating the HID lamp only when the light energy is directed toward the surgical site;
    d. monitoring an operation with a control responsive to temperatures of the HID lamp and the portable power supply, the control responding to a level of energy in the portable power supply, heat within the headlight source and electromagnet radiation supplying illumination, and
    e. extending the light cable between the HID lamp and a mount positioned on the head of a surgeon for aiming the illumination toward the surgical site for enhancing the color spectra of the visual field during surgery thereby providing the surgeon improved clarity in observation including depth of field and natural colorations during surgery.

11. The portable headlight assembly of claim 1 further comprising a belt attached to the housing to mount the portable headlight assembly to the practitioner.

12. The portable headlight assembly of claim 4, wherein the HID lamp meets UL requirements for maximum infrared or ultraviolet output per square centimeter.

13. The portable headlight assembly of claim 4, wherein, in use, a tip of the HID lamp has a tip temperature from 200 degrees C. to 285 degrees C.

* * * * *